(12) United States Patent
Wade et al.

(10) Patent No.: US 11,768,116 B2
(45) Date of Patent: *Sep. 26, 2023

(54) NONINVASIVE BLOOD PRESSURE SENSOR

(71) Applicant: Honeywell International Inc., Charlotte, NC (US)

(72) Inventors: Richard Wade, Worthington, OH (US); Ian Bentley, New Ipswich, NH (US)

(73) Assignee: HONEYWELL INTERNATIONAL INC., Charlottle, NC (US)

( * ) Notice: Subject to any disclaimer, the term of this patent is extended or adjusted under 35 U.S.C. 154(b) by 323 days.

This patent is subject to a terminal disclaimer.

(21) Appl. No.: 17/063,868

(22) Filed: Oct. 6, 2020

(65) Prior Publication Data
US 2021/0018384 A1    Jan. 21, 2021

Related U.S. Application Data (63) Continuation of application No. 16/366,194, filed on Mar. 27, 2019, now Pat. No. 10,830,653.

(51) Int. Cl.
| | |
|---|---|
| *G01L 1/26* | (2006.01) |
| *A61B 5/021* | (2006.01) |
| *G01L 1/18* | (2006.01) |
| *G01L 17/00* | (2006.01) |

(52) U.S. Cl.
CPC ............ *G01L 1/26* (2013.01); *A61B 5/02141* (2013.01); *G01L 1/18* (2013.01); *A61B 2562/028* (2013.01); *A61B 2562/0247* (2013.01); *G01L 17/005* (2013.01)

(58) Field of Classification Search
CPC . G01L 1/26; G01L 1/18; G01L 17/005; A61B 5/021411; A61B 2562/0247; A61B 2562/028
See application file for complete search history.

(56) References Cited

U.S. PATENT DOCUMENTS

| | | |
|---|---|---|
| 2,720,634 A | 10/1955 | Hart |
| 4,825,876 A | 5/1989 | Beard |
| 4,920,972 A * | 5/1990 | Frank ................... G01L 19/142 600/561 |

(Continued)

FOREIGN PATENT DOCUMENTS

| | | |
|---|---|---|
| CN | 101479581 A | 7/2009 |
| WO | 1998/047424 | 10/1998 |

OTHER PUBLICATIONS

Extended European Search Report for Patent Application No. 20165036.3 dated Jul. 3, 2020, 8 pages.

(Continued)

*Primary Examiner* — Jonathan M Dunlap
(74) *Attorney, Agent, or Firm* — Alston & Bird LLP (57) ABSTRACT

Example systems, apparatuses and methods are disclosed for sensing a force applied by an external source in a fluid monitoring tube. An example system comprises a force sensing device and signal conditioning circuitry configured to be electrically coupled to the force sensing device. The example system further comprises a housing configured to enclose the force sensing device and the signal conditioning circuitry. The housing comprises a snap structure configured to attach the housing to a base plate and retain the force sensing device and the signal conditioning circuitry in the housing.

17 Claims, 7 Drawing Sheets

(56) References Cited

U.S. PATENT DOCUMENTS

| | | | |
|---|---|---|---|
| 5,097,841 A | 3/1992 | Moriuchi et al. | |
| 5,184,107 A | 2/1993 | Maurer | |
| 5,410,916 A | 5/1995 | Cook | |
| 5,540,100 A | 7/1996 | von Berg | |
| 5,719,334 A | 2/1998 | Parsons | |
| 6,056,585 A | 5/2000 | Hatakeyama et al. | |
| 6,117,086 A | 9/2000 | Shulze | |
| 7,162,927 B1 | 1/2007 | Selvan et al. | |
| 7,430,918 B2 | 10/2008 | Selvan et al. | |
| 7,726,197 B2 | 6/2010 | Selvan et al. | |
| 7,880,103 B2 | 2/2011 | Bharaj et al. | |
| 8,186,226 B2 | 5/2012 | Ricks | |
| 8,215,176 B2 | 7/2012 | Ding et al. | |
| 8,230,743 B2 | 7/2012 | Wade et al. | |
| 8,312,774 B2 | 11/2012 | Bentley et al. | |
| 8,322,225 B2 | 12/2012 | Bentley et al. | |
| 8,757,001 B2 | 6/2014 | Wade et al. | |
| 9,003,897 B2 | 4/2015 | Wade et al. | |
| 9,003,899 B2 | 4/2015 | Wade | |
| 9,052,217 B2 | 6/2015 | Milley et al. | |
| 9,945,747 B1 | 4/2018 | Kusanale et al. | |
| 10,830,653 B2 | 11/2020 | Wade et al. | |
| 2002/0198458 A1 | 12/2002 | Tripp et al. | |
| 2004/0162521 A1 | 8/2004 | Bengtsson | |
| 2007/0197922 A1 | 8/2007 | Bradley et al. | |
| 2008/0053255 A1* | 3/2008 | Furey | G01D 11/30 73/866.5 |
| 2008/0127741 A1 | 6/2008 | Selvan et al. | |
| 2010/0206046 A1 | 8/2010 | Bentley et al. | |
| 2011/0005326 A1 | 1/2011 | Bentley et al. | |
| 2014/0130605 A1 | 5/2014 | Milley et al. | |
| 2016/0228016 A1 | 8/2016 | Naftalovitz et al. | |
| 2016/0231186 A1 | 8/2016 | Sood et al. | |
| 2017/0191895 A1 | 7/2017 | Eckhardt et al. | |
| 2018/0217018 A1 | 8/2018 | Eckhardt et al. | |

OTHER PUBLICATIONS

Non-Final Rejection dated Mar. 30, 2020 for U.S. Appl. No. 16/366,194.

Notice of Allowance and Fees Due (PTOL-85) dated Jul. 8, 2020 for U.S. Appl. No. 16/366,194.

Notice of Allowance and Fees Due (PTOL-85) dated Jul. 21, 2020 for U.S. Appl. No. 16/366,194.

EP Office Action dated Oct. 4, 2022 for EP Application No. 20165036.

CN Notice of Allowance, including Search Report, dated Jan. 5, 2023 for CN Application No. 202010227711.

English translation of CN Notice of Allowance dated Jan. 5, 2023 for CN Application No. 202010227711.

* cited by examiner

SECTION A-A

NONINVASIVE BLOOD PRESSURE SENSOR

CROSS-REFERENCE TO RELATED APPLICATIONS

This application is a continuation of U.S. patent application Ser. No. 16/366,194, filed Mar. 27, 2019, which is hereby incorporated herein by reference in its entirety.

TECHNOLOGICAL FIELD

Example embodiments of the present disclosure relate generally to sensors and, more particularly, to force sensors.

BACKGROUND

Industrial and commercial applications, including medical equipment, are increasingly utilizing force sensors to determine applied forces. However, conventional force sensor designs cannot be integrated easily and cost-effectively into disposable blood pressure monitoring devices.

Applicant has identified a number of deficiencies and problems associated with conventional force sensors. Through applied effort, ingenuity, and innovation, many of these identified problems have been solved by developing solutions that are included in embodiments of the present disclosure, many examples of which are described in detail herein.

SUMMARY

Systems, apparatuses, and methods (including, but not limited to methods of manufacturing and methods of packaging) are disclosed herein for providing a disposable blood pressure monitoring device having a miniature size force sensor package design with a gel-based coupling technology. In some embodiments, the miniature size force sensor package design provided herein solves the above problems by providing a coupling interface that enables the miniature size force sensor to be integrated easily and cost-effectively into various application areas and types of equipment, including disposable blood pressure monitoring devices.

In an example embodiment, a system is provided for sensing a force applied by an external source in a fluid monitoring tube. The system comprises a force sensing device and signal conditioning circuitry configured to be electrically coupled to the force sensing device. The system further comprises a housing configured to enclose the force sensing device and the signal conditioning circuitry. The housing comprises a snap structure configured to attach the housing to a base plate and retain the force sensing device and the signal conditioning circuitry in the housing.

In another example embodiment, an apparatus is provided for sensing a force applied by an external source in a fluid monitoring tube. The apparatus comprises a force sensing device and signal conditioning circuitry configured to be electrically coupled to the force sensing device. The apparatus further comprises a housing configured to enclose the force sensing device and the signal conditioning circuitry. The housing comprises a snap structure configured to attach the housing to a base plate and retain the force sensing device and the signal conditioning circuitry in the housing. Further, the housing defines an aperture configured to provide a coupling interface configured to provide a path for the force to be transferred to the force sensing device through a coupling. The apparatus further comprises the base plate.

In yet another example embodiment, a method is provided for manufacturing an apparatus for sensing a force applied by an external source in a fluid monitoring tube. The method comprises mounting a force sensing device on a surface of a substrate. The method further comprises mounting signal conditioning circuitry on the surface of the substrate. The method further comprises assembling a housing enclosing at least the force sensing device and the signal conditioning circuitry. The housing comprises a snap structure configured to retain the force sensing device and the signal conditioning circuitry in the housing. The method further comprises attaching the housing to a base plate using the snap structure.

The above summary is provided merely for purposes of summarizing some example embodiments to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which will be further described below.

BRIEF DESCRIPTION OF THE DRAWINGS

Having described certain example embodiments of the present disclosure in general terms above, reference will now be made to the accompanying drawings, which are not necessarily drawn to scale.

DETAILED DESCRIPTION

The following description should be read with reference to the drawings wherein like reference numerals indicate like elements throughout the several views. The detailed description and drawings show several embodiments which are meant to be illustrative of the disclosure. It should be understood that any numbering of disclosed features (e.g., first, second, etc.) and/or directional terms used in conjunction with disclosed features (e.g., front, back, under, above, etc.) are relative terms indicating illustrative relationships between the pertinent features.

It should be understood at the outset that although illustrative implementations of one or more aspects are illustrated below, the disclosed assemblies, systems, and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents. While values for dimensions of various elements are disclosed, the drawings may not be to scale.

The word "example," when used herein, is intended to mean "serving as an example, instance, or illustration." Any implementation described herein as an "example" is not necessarily preferred or advantageous over other implementations.

Generally, force sensors are used in a variety of applications such as, but not limited to, infusion pumps, ambulatory non-invasive pumps, occlusion detection, enteral pumps, load and compression sensing, variable tension control, and other application areas. Further, there is a continuous push from the market for reduction in size of the force sensors. Users in certain applications may need a force sensor which is small enough to fit into an application area and simultaneously provides an interface which is large enough for deployment. For instance, the disposable blood pressure monitoring market is a large volume market that exceeds volumes of 20 million pieces per year. In many instances, these disposable blood pressure monitoring devices must meet the specification and performance requirements of the BP22 standard for blood pressure transducers promulgated by the American National Standards Institute, Inc., and the Association for the Advancement of Medical Instrumentation. However, the disposable blood pressure monitoring market is placing increasing pressure to provide low cost solutions for sterilized, disposable blood pressure monitoring devices.

Existing disposable blood pressure monitoring devices typically consist of laser trimmed pressure sensors packaged into a standard housing assembly. The standard housing assembly has luer locks to engage tubing and is transparent to allow visibility to the blood flow. The standard housing assembly further mounts the sensor and provides an electrical cable output. However, these disposable blood pressure monitoring devices are too expensive to satisfy the market demand for increasingly low cost solutions for sterilized, disposable blood pressure monitoring devices.

The disclosure solves these problems by describing unique designs for disposable blood pressure monitoring devices that replace the conventional laser trimmed ceramic plate design, which drives the costs of these devices, with a small force sensing die that incorporates deep reactive-ion etching (DRIE) processing to minimize the size of the force sensing assembly and thereby minimize the overall size of the blood pressure monitoring device. The disclosure further solves these problems by describing a specialized solution that adjusts the bridge output of the force sensing device to correct for offset and span temperature effects. The disclosure further solves these problems by describing a design that assembles the force sensing device into the housing without a glue joint by assembling a radial seal ring structure in the housing to engage the outer diameter of the gel ring on the force sensing device to seal the force sensing device into the housing. The disclosure further describes using one or more snap structures disposed between the base plate and the housing to retain the force sensing assembly (e.g., the force sensing device, gel ring, gel, signal conditioning circuitry, substrate, and wire bonds) in the housing and sandwich the electrical cables against wedge terminals mounted to the backside of the substrate (e.g., a printed circuit board (PCB)) using surface-mount technology (SMT). These wedge terminals may act as springs to engage the electrical cables and create the electrical connection to external devices.

In some embodiments, the disclosure describes multiple levels of assembly. The first level of assembly may be directed to the force sensing assembly (e.g., the force sensing device, gel ring, gel, signal conditioning circuitry, substrate, and wire bonds), which may be manufactured using a PCB panel having four wedge terminals SMT mounted to each position on the panel. The PCB panel may be a very high density panel to lower the unit costs (e.g., greater than 500 positions one panel, and possibly as many as 1,500 positions on one panel). The force sensing device may comprise a pressure range gauge sense die adhesively attached to the PCB substrate and wire bonded to the PCB. In some embodiments, the pressure range gauge sense die may be a one bar pressure range gauge sense die. A digitally controlled resistor network may be adhesively attached to the PCB and wire bonded to the PCB. A gel ring (e.g., a metal ring) may be adhesively attached to the PCB around the sense die and wire bonds and filled with a biocompatible room-temperature vulcanizing (RTV) material, such as silicone. The force sensing assembly then may be packaged into tape and reel packaging for delivery to the final assembly line.

Final assembly may involve picking the force sensing assembly from the tape and reel packaging and placing the force sensing assembly into the housing by pressing the gel ring into the mating hole in the fluid monitoring tube of the housing. This press fit may seal the force sensing assembly into the housing. In some embodiments, the seal may propagated by another element with compliance specifically to seal between the bore and the sensor gel ring. The backside of the force sensing assembly PCB may comprise four wedge terminals, which may be exposed, allowing the force sensing assembly to receive an electrical cable harness (e.g., a wire harness) with stripped electrical cables which may mate into grooves in the housing. The grooves in the housing may help to align the electrical cables to the terminals on the PCB. The base plate may engage the housing and press the electrical cables against the terminals on the PCB. This base plate may also support, and in some instances push on, the PCB to hold the gel ring into the housing. The blood pressure monitoring device may be held together by one or more snap structures in the plastic of the base plate engaging mating structures in the housing, or vice versa. The one or more snap structures may be tight enough to hold the assembly together and keep the electrical contacts engaged for life of product, which in some instances may be two years of shelf storage and 3 days of operating use.

FIGS. 1A, 1B, 1C, and 1D illustrate an example top view, an example isometric view, an example cross-sectional view, and another example cross-sectional view A-A, respectively, of an example disposable blood pressure monitoring device 100 in accordance with some example embodiments described herein. The example disposable blood pressure monitoring device 100 may comprise any combination of components, structures, and features herein, including the addition, omission, or rearrangement of components, structures, and features. In some embodiments, the example disposable blood pressure monitoring device 100 may be a hardware device with embedded software configured to measure, detect, and transmit data (e.g., temperature, pressure, motion, and other suitable data). In some embodiments, the embedded software may be configured to run in an apparatus, device, or unit (e.g., firmware).

In some embodiments, as shown in FIGS. 1A, 1B, 1C, and 1D, the example disposable blood pressure monitoring device 100 may comprise a base plate 102 (e.g., a plastic base plate) attached (e.g., using one or more snap structures) to a housing 104 comprising a fluid monitoring tube, a luer lock 106, and a luer lock fitting 108. For example, the housing 104 may comprise a snap structure configured to attach the housing 104 to the base plate 102 and retain the force sensing device 110 and optional signal conditioning circuitry in the housing 104. In some embodiments, the one or more snap structures may be disposed between the base plate 102 and the housing 104 to retain the force sensing assembly in the housing 104 and sandwich the one or more electrical cables 114 against one or more wedge terminals that may be SMT mounted to the second surface 112b (e.g., backside) of the substrate 112. The one or more wedge terminals may act as springs to engage the one or more electrical cables 114 and create the electrical connection to external devices.

In some embodiments, the housing 104 may be optically transparent or near-transparent to allow for visual confirmation (e.g., by an imaging device or a user's eye) that no bubbles are present in the fluid in the fluid monitoring tube or that air bubbles have been cleared therefrom. In some embodiments, the base plate 102 may not be optically transparent or near-transparent. For example, the housing 104, the base plate 102, or both may be made of an optically transparent polymer or plastic.

In some embodiments, the example disposable blood pressure monitoring device 100 may further comprise a force sensing assembly comprising a force sensing device 110 (e.g., comprising a force sensing die, a gel ring, and a biocompatible RTV material such as a silicone gel), optional signal conditioning circuitry, wire bonds, and a substrate 112 (e.g., a PCB). The substrate 112 may comprise a first surface 112a (e.g., a top surface) and a second surface 112b (e.g., a bottom surface) opposite the first surface 112a. The force sensing device 110 may be configured to be disposed on the first surface 112a of the substrate. In some embodiments, the force sensing device 110 may be an analog force sensing device. In some embodiments, the force sensing device 110 may be a digital force sensing device. In some embodiments, the force sensing device 110 may comprise at least one of a piezoresistive force sensing device and a microelectromechanical systems (MEMS) force sensing device. In some embodiments, the force sensing die included in the force sensing device 110 may be a small force sensing die that incorporates DRIE processing to minimize the overall size of the force sensing assembly and thereby minimize the overall size of the example disposable blood pressure monitoring device 100.

In some embodiments, the housing 104 may be configured to enclose the force sensing device 110. For example, the housing 104 may define an aperture 113 configured to provide a coupling interface configured to provide a path for the force to be transferred to the force sensing device 110 through a coupling. In some embodiments, the center of the aperture 113 may be configured to align with a center of the force sensing device 110. In some embodiments, the coupling may be a gel-based coupling comprising a gel configured to transmit the force to the force sensing device. For example, the gel may be a biocompatible RTV material such as silicone. In some embodiments, the force sensing device 110 may be assembled into the housing 104 without a glue joint by, for example, assembling a radial seal ring structure in the housing 104 to engage the outer diameter of the gel ring on the force sensing device 110 to seal the force sensing device 110 into the housing 104.

In some embodiments, a plurality of electrical contact pads (e.g., four electrical contact pads) may be disposed on the second surface 112b of the substrate. In some embodiments, the example disposable blood pressure monitoring device 100 may further comprise electrical cables 114 (e.g., four electrical cables), an electrical cable harness 116, and an electrical connection terminal 118 (e.g., a six-pin plug). For example, the plurality of electrical contact pads may be, or may be attached to, a plurality of wedge terminals (e.g., four wedge terminals) configured to mechanically couple the plurality of electrical cables 114 to the plurality of electrical contact pads.

Figure 1A:
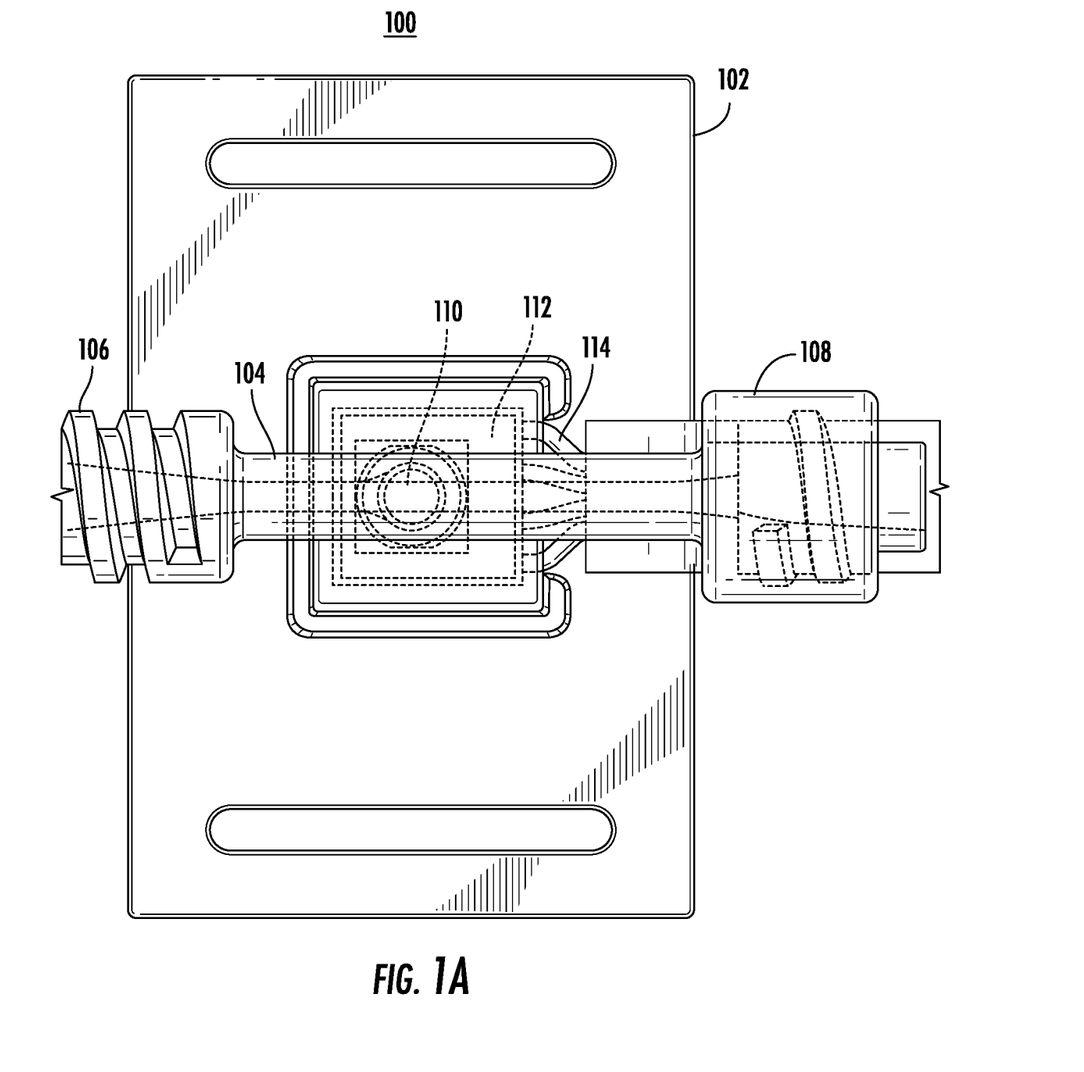
FIGS. 1A, 1B, 1C, and 1D respectively show an example top view, an example isometric view, an example cross-sectional view, and another example cross-sectional view of an example disposable blood pressure monitoring device in accordance with some example embodiments described herein.
Figure 1B:
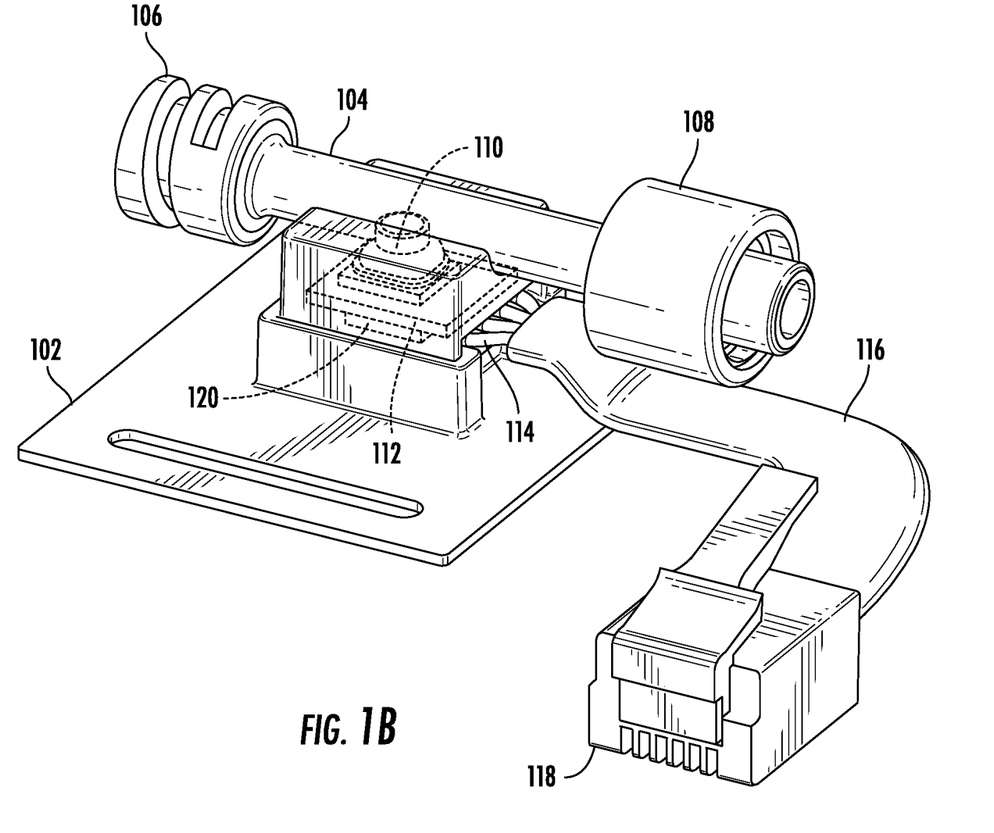
Figure 1C:
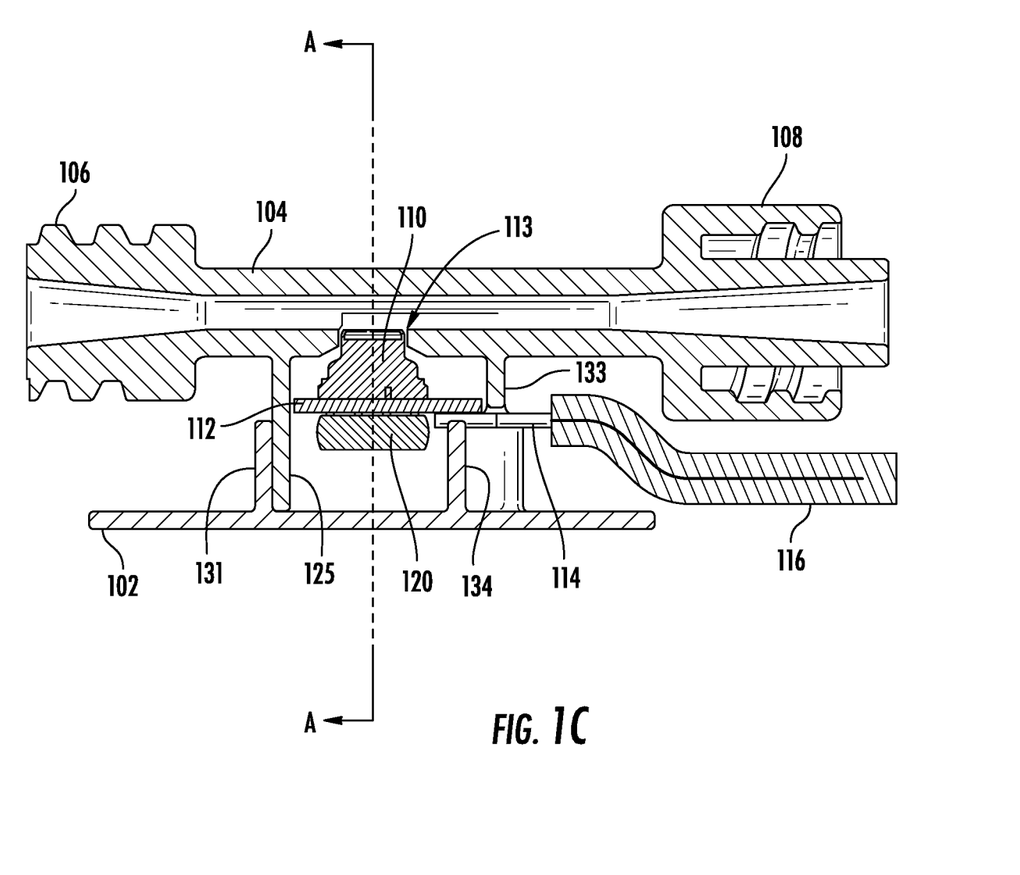

In some embodiments, as shown in FIG. 1C, the example disposable blood pressure monitoring device 100 may comprise a cable trap comprising one or more cable trap support structures configured to hold the electrical cables 114 against the substrate 112. For example, the base plate 102 may comprise a cable trap support structure 134 configured to engage the one or more electrical cables 114. In some instances, the cable trap support structure 134 on the base plate 102 may pinch the one or more electrical cables 114 against the one or more electrical contact pads disposed on the second surface 112b of the substrate 112 or the one or more wedge terminals attached thereto. In some instances, the cable trap support structure 134 on the base plate 102 may define a semi-circular notch for each of the one or more electrical cables 114. For example, the semi-circular notch may have a diameter substantially similar to the diameter of each of the one or more electrical cables 114. As a result, as shown in FIG. 1C, the lower half of each of the one or more electrical cables 114 may be cradled within each of the one or more semi-circular notches of the cable trap support structure 134 and only the upper half of each of the one or more electrical cables 114 may protrude above the cable trap support structure 134. In some embodiments, the housing 104 may comprise a cable trap support structure 133 configured to restrict upward movement of the one or more electrical cables 114 and to restrict lateral movement of the substrate 112.

In some embodiments, the base plate 102 may be attached to the housing 104 using an adhesive, one or more snap structures, any other suitable attachment mechanism (e.g., screws, fasteners), or a combination thereof. For example, housing 104 may comprise a downward-facing protrusion 125 configured to attach to an upward-facing protrusion 131 of the base plate 102. In some instances, as shown in FIGS. 1A, 1B, 1C, and 1D, the outward-facing surface of the downward-facing protrusion 125 of the housing 104 may be configured to be attached to the inward-facing surface of the upward-facing protrusion 131 of the base plate 102. In other instances, the inward-facing surface of the downward-facing protrusion 125 of the housing 104 may be configured to be attached to the outward-facing surface of the upward-facing protrusion 131 of the base plate 102.

In some embodiments, the downward-facing protrusion 125 of the housing 104 may be configured to be attached to the upward-facing protrusion 131 of the base plate 102 using an adhesive, such as a two-part epoxy resin. In some embodiments, the downward-facing protrusion 125 of the housing 104 may be configured to be attached to the upward-facing protrusion 131 of the base plate 102 using one or more snap structures. In some embodiments, the bottom of the outward-facing surface of the downward-facing protrusion 125 of the housing 104 may have an outward-facing protrusion, and the bottom of the inward-facing surface of the upward-facing protrusion 131 of the base plate 102 may have a notch or groove configured to receive the outward-facing protrusion 125 of the housing 104. As the outward-facing surface of the downward-facing protrusion 125 of the housing 104 is being inserted against the inward-facing surface of the upward-facing protrusion 131 of the base plate 102, the downward-facing protrusion 125 may be inwardly biased by the outward-facing protrusion of the downward-facing protrusion 125 contacting the inward-facing surface of the upward-facing protrusion 131 of the base plate 102. Once the outward-facing protrusion of the downward-facing protrusion 125 has been inserted into the notch or groove of the inward-facing surface of the upward-facing protrusion 131, the downward-facing protrusion 125 may snap outwardly to its original unbiased position, thereby locking the housing 104 into the base plate 102.

In some embodiments, the optional signal conditioning circuitry may be configured to be electrically coupled to the force sensing device 110 and the plurality of electrical contact pads, and the housing 104 may be further configured to enclose the optional signal conditioning circuitry. In some embodiments, as shown in FIGS. 1A, 1B, 1C, and 1D, where the force sensing device 110 is a digital force sensing device, a bottom surface of the optional signal conditioning circuitry may be configured to be disposed on the first surface 112a of the substrate 112, and the force sensing device 110 may be configured to be disposed on a top surface of the optional signal conditioning circuitry (e.g., the optional signal conditioning circuitry may be disposed between the force sensing device 110 and the substrate 112). In some embodiments, where the force sensing device 110 is either an analog force sensing device or a digital force sensing device, the optional signal conditioning circuitry may be configured to be disposed on the first surface 112a of the substrate separate from the force sensing device 110 (e.g., as arranged in FIG. 2B). In some embodiments, the optional signal conditioning circuitry may be configured to adjust the bridge output of the force sensing device 110 to correct for offset and span temperature effects.

Figure 1D:
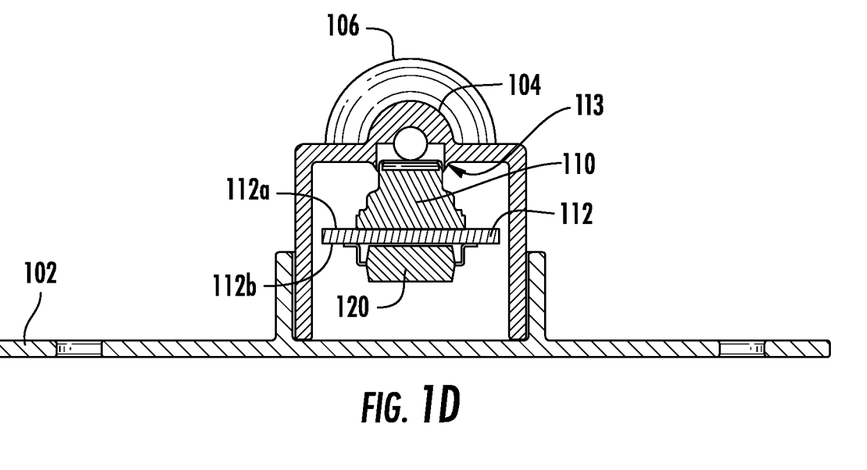

In some embodiments, the example disposable blood pressure monitoring device 100 may comprise a digitally controlled resistor network 120. For example, the digitally controlled resistor network 120 may comprise electrically erasable programmable read-only memory (EEPROM) circuitry configured to the particular requirements of the force sensing assembly, the example disposable blood pressure monitoring device 100, or both. In some embodiments, the digitally controlled resistor network 120 may be an encryption memory storage to prevent counterfeit sensors from working with the example disposable blood pressure monitoring device 100. In some embodiments, the digitally controlled resistor network 120 may be a digital encryption device. In some embodiments, the digitally controlled resistor network 120 may be an analog encryption device. In some embodiments, as shown in FIGS. 1B, 1C, and 1D, the digitally controlled resistor network 120 may be disposed on the second surface 112b (e.g., the backside or terminal side) of the substrate 112.

Figure 2A:
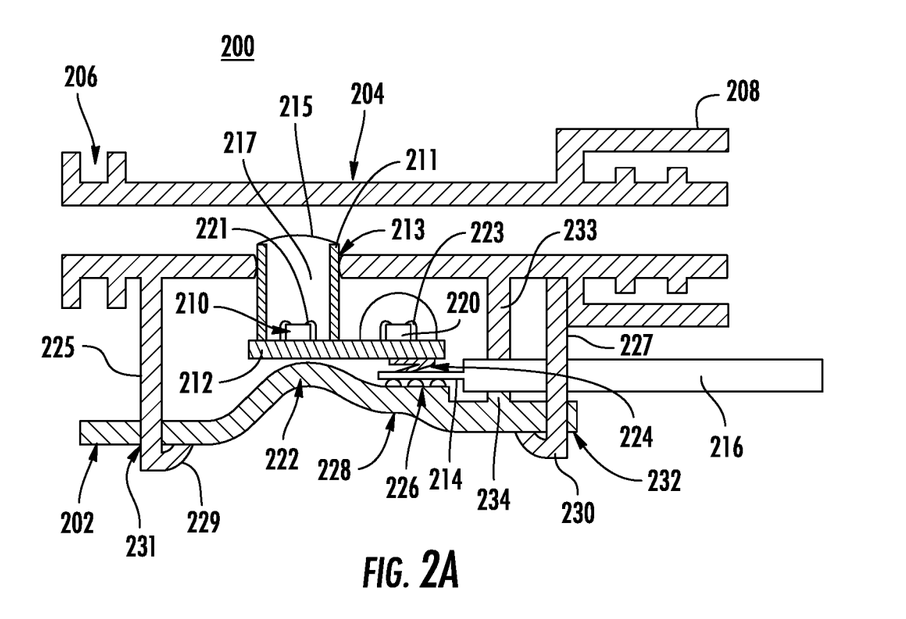
FIG. 2A shows an example cross-sectional view of another example disposable blood pressure monitoring device in accordance with some example embodiments described herein.

FIG. 2A shows an example cross-sectional view of an example disposable blood pressure monitoring device 200 in accordance with some example embodiments described herein. In some embodiments, as shown in FIG. 2A, the example disposable blood pressure monitoring device 200 may comprise a base plate 202 (e.g., a plastic base plate) attached to a housing 204 comprising a fluid monitoring tube, a luer lock 206, and a luer lock fitting 208. In some embodiments, the housing 204 may comprise one or more snap structures (e.g., snap structure 225, snap structure 227, or both) configured to attach the housing 204 to the base plate 202 and retain a force sensing device 210 and an optional signal conditioning circuitry 220 in the housing 204.

In some embodiments, the base plate 202 may be attached to the housing 204 using one or more snap structures, such as a snap structure 225 and a snap structure 227. In some embodiments, the force sensing assembly may be retained in the housing 204 by the snap structure 225 and the snap structure 227. In some embodiments, the snap structure 225 and the snap structure 227 may be disposed between the base plate 202 and the housing 204 to retain the force sensing assembly in the housing 204 and sandwich the one or more electrical cables 214 against the one or more wedge terminals 224 that may be SMT mounted to the second surface 212b (e.g., backside) of the substrate 212. The one or more wedge terminals 224 may act as springs to engage the one or more electrical cables 214 and create the electrical connection to external devices.

In some embodiments, the snap structure 225 may be a flexible arm (e.g., cantilever) connected to the housing 204 at the top end of the flexible arm and having an inward-facing protrusion 229 at the bottom end of the flexible arm. The base plate 202 may have an opening 231 configured to receive the snap structure 225. As the snap structure 225 is being inserted into the opening 231 in the base plate 202, the snap structure 225 may be outwardly biased by the inward-facing protrusion 229 contacting the inward-facing side of the opening 231. Once the inward-facing protrusion 229 of the snap structure 225 has been inserted into the opening 231 in the base plate 202, the snap structure 225 may snap inwardly to its original unbiased position, thereby locking the housing 204 into the base plate 202.

In some embodiments, the snap structure 227 may be a flexible arm (e.g., cantilever) connected to the housing 204 at the top end of the flexible arm and having an inward-facing protrusion 230 at the bottom end of the flexible arm. The base plate 202 may have an opening 232 configured to receive the snap structure 227. As the snap structure 227 is being inserted into the opening 232 in the base plate 202, the snap structure 227 may be outwardly biased by the inward-facing protrusion 230 contacting the inward-facing side of the opening 232. Once the inward-facing protrusion 230 of the snap structure 227 has been inserted into the opening 232 in the base plate 202, the snap structure 227 may snap inwardly to its original unbiased position, thereby locking the housing 204 into the base plate 202.

In some embodiments, the housing 204 may be optically transparent or near-transparent to allow for visual confirmation (e.g., by an imaging device or a user's eye) that no bubbles are present in the fluid in the fluid monitoring tube or that air bubbles have been cleared therefrom. In some embodiments, the base plate 202 may not be optically transparent or near-transparent. For example, the housing 204 may be made of an optically transparent polymer or plastic while the base plate 202 may be made of a non-optically transparent polymer or plastic.

In some embodiments, the example disposable blood pressure monitoring device 200 may further comprise a force sensing assembly comprising a force sensing device 210 (e.g., comprising a force sensing die, a gel ring 211, and a gel 217 (e.g., a biocompatible RTV material such as a silicone gel) having a gel surface 215), wire bonds 221, optional signal conditioning circuitry 220, wire bonds 223, and a substrate 212 (e.g., a PCB). The substrate 212 may comprise a first surface 212a (e.g., a top surface) and a second surface 212b (e.g., a bottom surface) opposite the first surface 212a.

In some embodiments, the gel 217 forms a gel surface 215 at the sharp top surface of the gel ring 211 so that the force from the external source may be concentrated through the gel 217 directly to the force sensing device 210. In some embodiments, the gel surface 215 may be a domed or convex-shaped gel surface to avoid bubbles getting stuck in the fluid monitoring tube during fluid flow. For instance, in some embodiments a concave gel surface may create a low velocity zone in the fluid flow path and this low velocity zone could become a bubble trap. In some embodiments, a domed or convex-shaped gel surface may protrude slightly into the fluid flow path so as to allow for higher velocity zones in the fluid flow path and thereby decrease the occurrence of bubble traps without creating bubble traps at the edges.

In some embodiments, the gel 217 may be poured in the gel ring 211. As the gel 217 reaches the sharp top surface of the gel ring 211, the gel 217 stops and beads-up, resulting in the formation of the gel surface 215 (e.g., a domed or convex-shaped gel surface) of the gel 217 at the periphery of the aperture 213. For example, surface tension effects, adhesion effects, or both may account for the formation of the gel surface 215 (e.g., a domed or convex-shaped gel surface) of the gel 217 at the periphery of the sharp top surface of the gel ring 211. In some embodiments, the gel 217 may be a liquid gel. In other embodiments, the gel 217 may be a semi-liquid gel. In one example embodiment, the gel 217 may be a dielectric gel. In another example embodiment, the gel 217 may be a non-dielectric gel. In some embodiments, the gel 217 may be a silicone-based gel. It should be appreciated that, the gel 217 is only one example of the actuator, and it is contemplated that other suitable actuators may be used.

In some embodiments, the optional signal conditioning circuitry 220 may configured to be electrically coupled to the force sensing device 210 by one or more wire bonds. For example, the optional signal conditioning circuitry 220 may be configured to be electrically coupled to the substrate 212 by one or more wire bonds 223, the force sensing device 210 may be configured to be electrically coupled to the substrate 212 by one or more wire bonds 221, and the optional signal conditioning circuitry 220 may be configured to be electrically coupled to the force sensing device 210 through the substrate 212. In other embodiments, the electrical connections may be solder bumps or use other electrical joining techniques, such as through silicon vias with solder bumps or thermosonic ball bump welds, which may provide a space improvement. In some embodiments, the optional signal conditioning circuitry 220 may be configured to adjust the bridge output of the force sensing device 210 to correct for offset and span temperature effects.

In some embodiments, the force sensing device 210 may be configured to be disposed on the first surface 212a of the substrate. In some embodiments, the force sensing device 210 may be an analog force sensing device. In some embodiments, the force sensing device 210 may be a digital force sensing device. In some embodiments, the force sensing device 210 may comprise at least one of a piezoresistive force sensing device and a MEMS force sensing device. In some embodiments, the force sensing die included in the force sensing device 210 may be a small force sensing die that incorporates DRIE processing to minimize the overall size of the force sensing assembly and thereby minimize the overall size of the example disposable blood pressure monitoring device 200.

In some embodiments, the housing 204 may be configured to enclose the force sensing device 210. For example, the housing 204 may define an aperture 213 configured to provide a coupling interface configured to provide a path for the force (e.g., the force applied by an external source (e.g., blood) in the fluid monitoring tube of the housing 204) to be transferred to the force sensing device 210 through a coupling (e.g., gel 217 disposed in gel ring 211 and having a gel surface 215). In some embodiments, the aperture 213 defined in the housing 204 may have, for example, a circular, elliptical, oval, or polygonal cross-section. In some embodiments, the aperture 213 may have a cross-sectional radius, such as, but not limited to, 1.44 mm, 1.54 mm, 1.64 mm, or any other suitable radius. In some embodiments, the center of the aperture 213 may be configured to align with a center of the force sensing device 210. In some embodiments, the coupling may be a gel-based coupling comprising a gel 217 comprising a gel surface 215 and configured to transmit the force to the force sensing device 210. For example, the gel 217 may be a biocompatible RTV material such as silicone. In other embodiments, the coupling may be a mechanical coupling such as a stainless steel ball, an aluminum ball, or any other suitable mechanical coupling. In some embodiments, the force sensing device 210 may be assembled into the housing 204 without a glue joint by, for example, assembling a radial seal ring structure (e.g., the aperture 213) in the housing 204 to engage the outer diameter of the gel ring 211 on the force sensing device 210 to seal the force sensing device 210 into the housing 204.

In some embodiments, a plurality of electrical contact pads (e.g., four electrical contact pads) may be disposed on the second surface 212b of the substrate. In some embodiments, the example disposable blood pressure monitoring device 200 may further comprise electrical cables 214 (e.g., four electrical cables), an electrical cable harness 216, and an electrical connection terminal 218 (e.g., a six-pin plug). For example, the plurality of electrical contact pads may be, or may be attached to, a plurality of wedge terminals 224 (e.g., four wedge terminals) configured to mechanically couple the plurality of electrical cables 214 to the plurality of electrical contact pads.

In some embodiments, the example disposable blood pressure monitoring device 100 may comprise a digitally controlled resistor network. For example, the digitally controlled resistor network may comprise EEPROM circuitry configured to the particular requirements of the force sensing assembly.

In some embodiments, the optional signal conditioning circuitry 220 may be configured to be electrically coupled to the force sensing device 210 and the plurality of electrical contact pads, and the housing 204 may be further configured to enclose the optional signal conditioning circuitry 220. In some embodiments, where the force sensing device 210 is either an analog force sensing device or a digital force sensing device, the optional signal conditioning circuitry 220 may be configured to be disposed on the first surface 212a of the substrate. In some embodiments, where the force sensing device 210 is a digital force sensing device, the optional signal conditioning circuitry 220 may be configured to be disposed on the first surface 212a of the substrate 212, and the force sensing device 210 may be configured to be disposed on a top surface of the optional signal conditioning circuitry 220 (e.g., the optional signal conditioning circuitry 220 may be disposed beneath the force sensing device 210 or otherwise between the force sensing device 210 and the substrate 212).

In some embodiments, the base plate 102 may comprise a push structure 222 to push on the substrate 212 to hold the gel ring 211 into the housing 204. In some embodiments, the substrate 212 may further comprise one or more wedge terminals 224 that have been SMT mounted to the second surface 212b of the substrate 212. In some embodiments, the base plate 202 may further comprise one or more cable wire guides configured to support (e.g., hold in place) the one or more electrical cables that engage the one or more wedge terminals 224. The wedge terminals 224 (e.g., four wedge terminals) may be configured to act as springs to engage the electrical cables 214 (e.g., four electrical wires), which may also be pushed on and retained in place by the push structures 226 and the push structure 228.

In some embodiments, the housing 204 may comprise a strain relief support structure 233 configured to engage the electrical cable harness 216, which may also be engaged by an opposing strain relief support structure 234 on the base plate 202. For example, the strain relief support structure 233 on the housing 204 and the opposing strain relief support structure 234 on the base plate 202 may pinch the electrical cable harness 216 to provide strain relief.

Figure 2B:
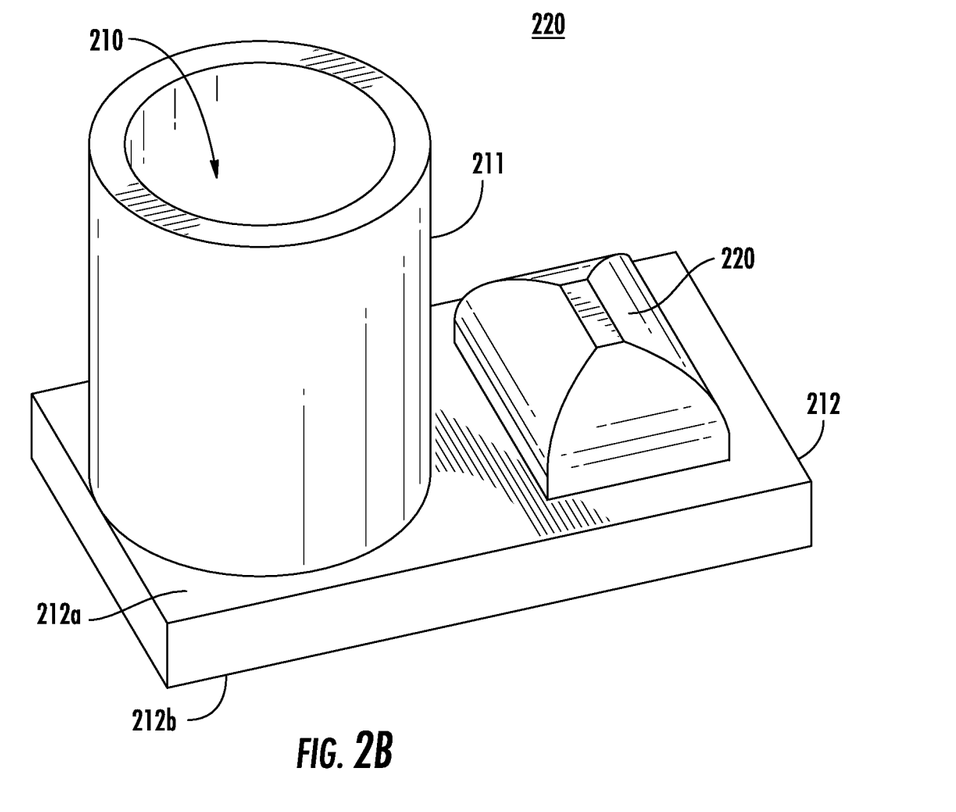
FIG. 2B shows an example isometric view of an example force sensing assembly in accordance with some example embodiments described herein.

As shown in FIG. 2B, the force sensing assembly of the example disposable blood pressure monitoring device 200 may comprise the force sensing device 210, the optional signal conditioning circuitry 220 (or, alternatively, the digitally controlled resistor network, or both), and a substrate 212. In some embodiments (not shown in FIG. 2B), the optional signal conditioning circuitry 220 may be disposed within the gel 217 (e.g., near or beneath the force sensing device 210). In other embodiments, as shown in FIG. 2B, the optional signal conditioning circuitry 220 may be disposed outside the gel 217 to provide the advantage of keeping the wire bonds 223 for the optional signal conditioning circuitry 220 out of the working path. In some instances, wire bonds disposed under the gel 217 may fatigue fail sooner than wire bonds that are not exposed to pressure or motion. By disposing the optional signal conditioning circuitry 220 outside of the gel 217, this failure mode may be advantageously avoided. Additionally, disposing the optional signal conditioning circuitry 220 outside of the gel 217 provides for more flexible signal conditioning circuitry upgrade techniques to incorporate improvements in sensing or signal processing technologies.

In some embodiments, the force sensing device 210 may comprise a force sensing die, a gel ring 211, and a gel 217 disposed on the first surface 212a (e.g., a top surface) of the substrate 212. The gel ring 211 may be made of metal (e.g., aluminum, stainless steel) or plastic (e.g., liquid crystal polymer (LCP), polyphenylene sulfide (PPS), LCP/PPS, or any other suitable material) and affixed to the substrate 212 using an adhesive, such as a two-part epoxy resin. The gel ring 211 may be cylindrical in profile and may have 90 degree corners at the top surface of the gel ring 211 to provide a 360 degree seal between the gel surface 215 of the gel 217 and the top surface of the gel ring 211. In some embodiments, the optional signal conditioning circuitry 220 (or, alternatively, the digitally controlled resistor network, or both) may be covered with a glob top over the wire bonds 223 to provide protection during handling and shipping.

In some embodiments, the force sensing device 210, the gel ring 211, the optional signal conditioning circuitry 220, or a combination thereof may be mounted on the first surface 212a of the substrate 212 using an adhesive. In some embodiments, the adhesive may comprise one or more of silicone, RTV silicone, a silicone-epoxy, a soft epoxy, a regular or hard epoxy, or any combination thereof. In one example embodiment, the adhesive may comprise a conductive adhesive. In another example embodiment, the adhesive may comprise a non-conductive adhesive or any combination of the conductive and the non-conductive adhesive. It should be appreciated that, the adhesive is only one example of a suitable bonding mechanism, and it is contemplated that other bonding mechanisms (e.g., but not limited to, solder eutectic, etc.) may be used.

In some embodiments, the substrate 212 may comprise a PCB. In other embodiments, the substrate 212 may comprise any suitable material, such as, but not limited to, a dielectric material, an insulating material, or any combination thereof. In one example embodiment, the substrate 212 may be a polygon in planar shape, such as, but not limited to, square, rectangle, triangle, pentagon, or any other suitable shape. In another example embodiment, the substrate 212 may be a non-polygon in planar shape. In some embodiments, the substrate 212 may be about 1.65 millimeters (mm)×1.65 mm in planar size. In other embodiments, the substrate 212 may have other suitable dimensions. In one example embodiment, the substrate 212 may be about 200 micrometers (microns) thick. In another example embodiment, the thickness of the substrate 212 may be about 300 microns, about 400 microns, about 600 microns, or any other suitable thickness.

In some embodiments, the electrical contact pads may correspond to metallic pads comprising one or more metals, for example, copper (Cu), silver (Ag), gold (Au), aluminum (Al), or a combination thereof. In one example embodiment, the electrical contact pads may be surface mounted on the second surface 212b of the substrate 212 using surface-mount technology (SMT). In another example embodiment, the electrical contact pads may be chemically disposed on the second surface 212b of the substrate 212 using a chemical process, such as, but not limited to, using a metal plating solution (such as copper plating solution) to deposit the metal on the second surface 212b of the substrate 212 to form the electrical contact pads. In yet another example embodiment, the electrical contact pads may be disposed through a process of etching on the second surface 212b of the substrate 212. In other example embodiments, the electrical contact pads may be disposed on the first surface 212a of the substrate 212.

In some embodiments, each of the electrical contact pads may be a polygon in planar shape, for example, triangle, rectangle, square, pentagon, hexagon, or any other suitable shape. In other embodiments, the electrical contact pads may be a non-polygon in planar shape. In some embodiments, each of the electrical contact pads may be about 1.30 mm×1.00 mm in planar size. In other embodiments, each of the electrical contact pads may comprise any suitable planar size, such as, but not limited to 1.23 mm×0.95 mm, 1.35 mm×1.05 mm, 1.58 mm×0.75 mm, 1.63 mm×0.80 mm, 1.68 mm×0.85 mm, or any other suitable planar size. In some embodiments, the electrical contact pads may be configured to provide an electrical connection with an external circuitry. The electrical contact pads may use a communication protocol to communicate with, and provide an electrical connection to, the external circuitry. For example, the communication protocol may include an Inter-Integrated Circuit (I2C) protocol, a Serial Peripheral Interface (SPI) protocol, or other communication protocols.

In some embodiments, the optional signal conditioning circuitry 220 is configured to even out variations in an input signal to make it suitable for further processing. The variations may arise due to factors such as, but not limited to, temperature variations, external noise, electromagnetic variations, other variations, or combinations thereof. In some embodiments, the optional signal conditioning circuitry 220 may comprise an application-specific integrated circuit (ASIC), an instrumentation amplifier, a microprocessor, a microcontroller, or a combination thereof. In some embodiments, the optional signal conditioning circuitry 220 may further comprise a digital amplifier with a built-in temperature sensor (not shown) for compensating temperature induced changes caused by the temperature variations.

In some embodiments, the optional signal conditioning circuitry 220 may be about 1.97 mm×1.52 mm in planar size. In other embodiments, the optional signal conditioning circuitry 220 may comprise any suitable planar size, such as, but not limited to, 1.50 mm×1.50 mm, 1.94 mm×1.47 mm, 2.00 mm×1.55 mm, or any other suitable planar size. In one example embodiment, the optional signal conditioning circuitry 220 may be about 0.36 mm thick. In another example embodiment, the thickness of the optional signal conditioning circuitry 220 may be about 0.35 mm, 0.36 mm, or any other suitable thickness.

In some embodiments, the optional signal conditioning circuitry 220 may be mounted on the first surface 212a of the substrate 212 using an adhesive. The optional signal conditioning circuitry 220 may be electrically coupled to the force sensing device 210 via one or more wire bonds such as wire bonds 221 and wire bonds 223. The wire bonds 221 and the wire bonds 223 may comprise one or more metals, for example, aluminum (Al), copper (Cu), gold (Au), silver (Ag), or a combination thereof. The wire bonds 221 and the wire bonds 223 may be wire bonded through suitable wire bonding techniques, for example, thermosonic bonding, ultrasonic bonding, thermocompression bonding, or a combination of such techniques. In some embodiments, each of the wire bonds 221 and the wire bonds 223 may have a thickness of about 25 microns. In other embodiments, each of the wire bonds 221 and the wire bonds 223 may have any other suitable thickness. It should be appreciated that, wire bonds are only one example of establishing an electrical connection between the force sensing device 210 and the optional signal conditioning circuitry 220, and it is contemplated that the optional signal conditioning circuitry 220 may be electrically connected to the force sensing device 210 via other ways such as, but not limited to, trace conductors, conductive elastomer pre-forms, conductive adhesives, anisotropic conductive adhesives, any other suitable connection, or a combination thereof.

In some embodiments, the optional signal conditioning circuitry 220 is electrically connected to the force sensing device 210. In operation, the optional signal conditioning circuitry 220 is configured to receive the output signal of the force sensing device 210, the optional signal conditioning circuitry 220 performs conditioning on the received output signal and further, provides a conditioned output signal for further processing. In some embodiments, the optional signal conditioning circuitry 220 may be disposed on the first surface 212a of the substrate 212 separately from the force sensing device 210. In other embodiments, the optional signal conditioning circuitry 220 may be disposed on the first surface 212a of the substrate 212 as a part of the force sensing device 210. In some embodiments, the optional signal conditioning circuitry 220 may be disposed on top of the force sensing device 210 and another circuitry may be disposed underneath the force sensing device 210 to provide additional features on the serial bus or analog signal path.

Figure 3:
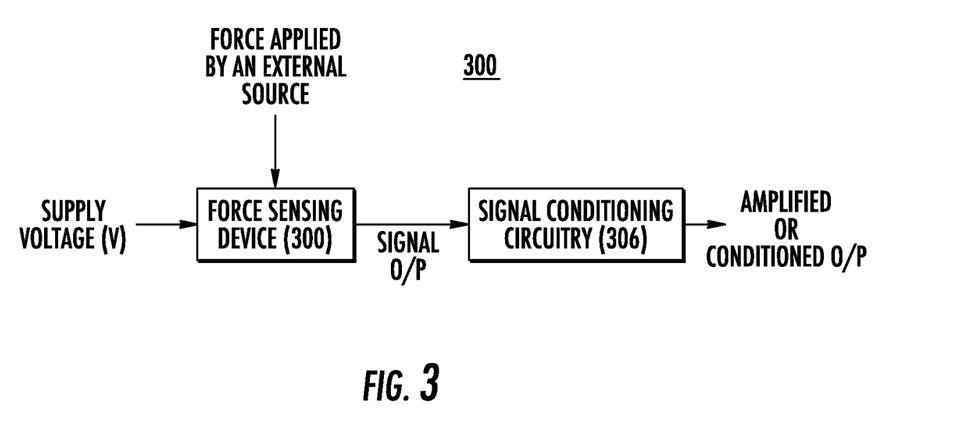
FIG. 3 shows a functional block diagram illustrating a method of operation of an example disposable blood pressure monitoring device in accordance with some example embodiments described herein.

FIG. 3 shows a functional block diagram 300 illustrating a method of operation of an example disposable blood pressure monitoring device (e.g., example disposable blood pressure monitoring device 100, example disposable blood pressure monitoring device 200) in accordance with some example embodiments described herein. The example disposable blood pressure monitoring device may be connected to an external circuitry (not shown) through the electrical contact pads. The force sensing device (e.g., force sensing device 110, force sensing device 210) and the optional signal conditioning circuitry (e.g., optional signal conditioning circuitry 220) may be connected via wire bonds and a substrate (e.g., substrate 112, 212). In operation, an external power source may supply a power voltage to the force sensing device via the electrical contact pads. The actuator (e.g., gel 217) may exert a force against the force sensing device in response to receiving the force from an external source. The actuator may transfer the force to the force sensing device causing deflection in an electrical resistance of the force sensing device. The deflection in the electrical resistance may cause a change in an output signal of the force sensing device. This change in the output signal is an indication or measurement of the force applied by the external source. The optional signal conditioning circuitry may receive the change in the output signal and condition the received output signal.

Having described specific components, structures, and features of example devices that may carry out some functionality of the system described herein, example embodiments of the present disclosure are described below in connection with FIG. 4.

Figure 4:
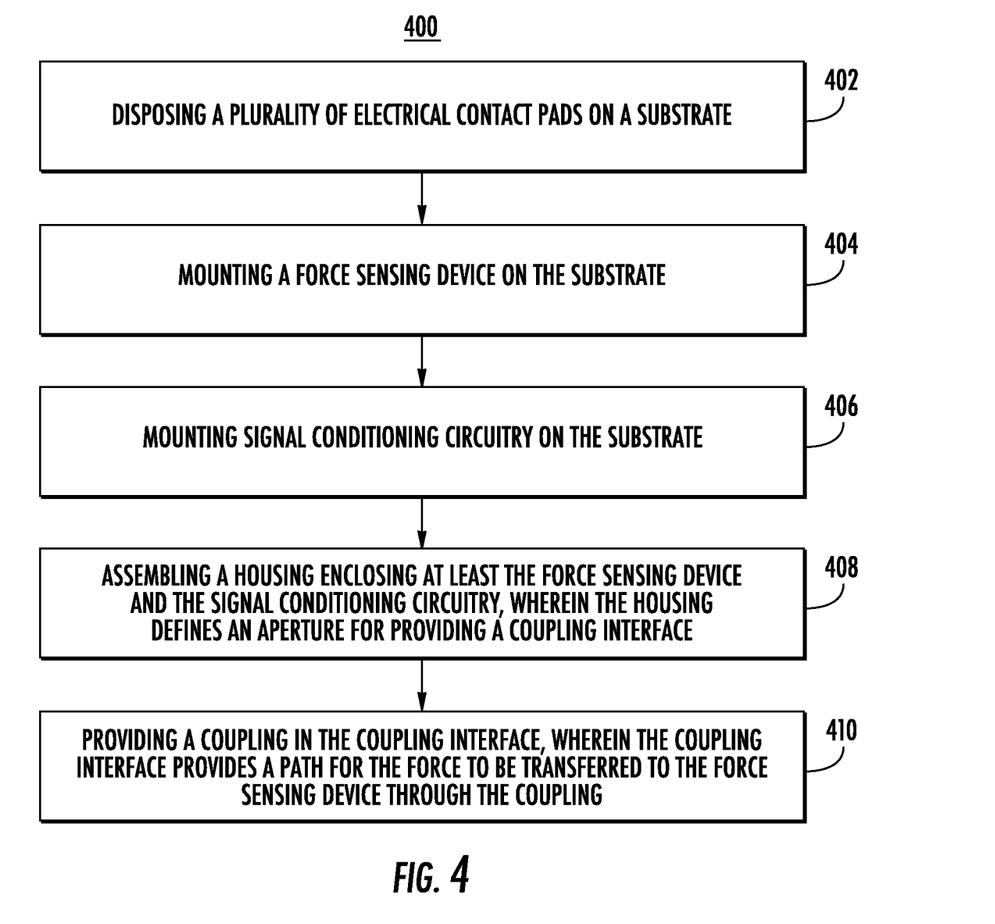
FIG. 4 shows a flowchart illustrating example operations for providing an example disposable blood pressure monitoring device in accordance with some example embodiments described herein.

FIG. 4 shows a flowchart 400 illustrating example operations for providing an example disposable blood pressure monitoring device in accordance with some example embodiments described herein. As shown by operation 402, the example flowchart 400 may begin by disposing a plurality of electrical contact pads on a second surface (e.g., second surface 112b, second surface 212b) of a substrate (e.g., substrate 112, substrate 212). The substrate may comprise a first surface (e.g., first surface 112a, first surface 212a) opposite the second surface. As shown by operation 404, the example flowchart 400 may proceed to mounting a force sensing device (e.g., force sensing device 110, force sensing device 210) on the first surface of the substrate. As shown by operation 406, the example flowchart 400 may proceed to mounting signal conditioning circuitry (e.g., optional signal conditioning circuitry 220) on the first surface of the substrate. As shown by operation 408, the example flowchart 400 may proceed to assembling a housing (e.g., housing 104, housing 204) enclosing at least the force sensing device and the signal conditioning circuitry. The housing may define an aperture (e.g., aperture 213) for providing a coupling interface. As shown by operation 410, the example flowchart 400 may proceed to providing a coupling (e.g., gel 217 disposed in gel ring 211) in the coupling interface. The coupling interface may provide a path for the force to be transferred to the force sensing device through the coupling. Optionally (not shown in FIG. 4), wherein the housing comprises a snap structure configured to retain the force sensing device and the signal conditioning circuitry in the housing, the example flowchart 400 may proceed to providing attaching the housing to a base plate using the snap structure.

In some embodiments, operations 402, 404, 406, and 408 may not necessarily occur in the order depicted in FIG. 4. In some embodiments, one or more of the operations depicted in FIG. 4 may occur substantially simultaneously. In some embodiments, one or more additional operations may be involved before, after, or between any of the operations shown in FIG. 4.

As described above, FIG. 4 illustrates an example flowchart describing operations performed in accordance with example embodiments of the present disclosure. It will be understood that each block of the flowchart, and combinations of blocks in the flowchart, may be implemented by various means, such as devices comprising hardware, firmware, one or more processors, and/or circuitry associated with execution of software comprising one or more computer program instructions. For example, one or more of the procedures described above may be performed by material handling equipment (e.g., a robotic arm, servo motor, motion controllers, and the like) and computer program instructions residing on a non-transitory computer-readable storage memory. In this regard, the computer program instructions which embody the procedures described above may be stored by a memory of an apparatus employing an embodiment of the present disclosure and executed by a processor of the apparatus. As will be appreciated, any such computer program instructions may be loaded onto a computer or other programmable apparatus (e.g., hardware) to produce a machine, such that the resulting computer or other programmable apparatus provides for implementation of the functions specified in the flowchart blocks. When executed, the instructions stored in the computer-readable storage memory produce an article of manufacture configured to implement the various functions specified in flowchart blocks. Moreover, execution of a computer or other processing circuitry to perform various functions converts the computer or other processing circuitry into a particular machine configured to perform an example embodiment of the present disclosure.

Accordingly, the described flowchart blocks support combinations of means for performing the specified functions and combinations of operations for performing the specified functions. It will also be understood that one or more flowchart blocks, and combinations of flowchart blocks, can be implemented by special purpose hardware-based computer systems which perform the specified functions, or combinations of special purpose hardware that execute computer instructions. For example, in one or more example embodiments, the functions described herein may be implemented by special-purpose hardware or a combination of hardware programmed by firmware or other software. In implementations relying on firmware or other software, the functions may be performed as a result of execution of one or more instructions stored on one or more non-transitory computer-readable media and/or one or more non-transitory processor-readable media. These instructions may be embodied by one or more processor-executable software modules that reside on the one or more non-transitory computer-readable or processor-readable storage media. Non-transitory computer-readable or processor-readable storage media may in this regard comprise any storage media that may be accessed by a computer or a processor. By way of example but not limitation, such non-transitory computer-readable or processor-readable media may comprise RAM, ROM, EEPROM, FLASH memory, disk storage, magnetic storage devices, or the like. Disk storage, as used herein, comprises compact disc (CD), laser disc, optical disc, digital versatile disc (DVD), floppy disk, and Blu-ray Disc™, or other storage devices that store data magnetically or optically with lasers. Combinations of the above types of media are also included within the scope of the terms non-transitory computer-readable and processor-readable media. Additionally, any combination of instructions stored on the one or more non-transitory processor-readable or computer-readable media may be referred to herein as a computer program product.

In some example embodiments, certain ones of the operations herein may be modified or further amplified as described below. Moreover, in some embodiments additional optional operations may also be included. It should be appreciated that each of the modifications, optional additions or amplifications described herein may be included with the operations herein either alone or in combination with any others among the features described herein.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," and similar words are not intended to limit the order of the steps; these words are simply used to guide the reader through the description of the methods. Further, any reference to claim elements in the singular, for example, using the articles "a," "an" or "the," is not to be construed as limiting the element to the singular and may, in some instances, be construed in the plural.

As described above and with reference to FIGS. 1-4, example embodiments of the present disclosure thus provide for an example disposable blood pressure monitoring device. Thus, the example disposable blood pressure monitoring device disclosed herein may easily and cost-effectively meet all of the performance requirements and also be sufficiently sensitive to detect a blood pressure.

While various embodiments in accordance with the principles disclosed herein have been shown and described above, modifications thereof may be made by one skilled in the art without departing from the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present disclosure. Furthermore, any advantages and features described above may relate to specific embodiments, but shall not limit the application of such issued claims to processes and structures accomplishing any or all of the above advantages or having any or all of the above features.

In addition, the section headings used herein are provided for consistency with the suggestions under 47 C.F.R. § 1.77 or to otherwise provide organizational cues. These headings shall not limit or characterize the disclosure set out in any claims that may issue from this disclosure. For instance, a description of a technology in the "Background" is not to be construed as an admission that certain technology is prior art to any disclosure in this disclosure. Neither is the "Summary" to be considered as a limiting characterization of the disclosure set forth in issued claims. Furthermore, any reference in this disclosure to "disclosure" or "embodiment" in the singular should not be used to argue that there is only a single point of novelty in this disclosure. Multiple embodiments of the present disclosure may be set forth according to the limitations of the multiple claims issuing from this disclosure, and such claims accordingly define the disclosure, and their equivalents, that are protected thereby. In all instances, the scope of the claims shall be considered on their own merits in light of this disclosure, but should not be constrained by the headings set forth herein.

Also, techniques, systems, subsystems, and methods described and illustrated in the various embodiments as discrete or separate may be combined or integrated with other systems, modules, techniques, or methods without departing from the scope of the present disclosure. Other devices or components shown or discussed as coupled to, or in communication with, each other may be indirectly coupled through some intermediate device or component, whether electrically, mechanically, or otherwise. Other examples of changes, substitutions, and alterations are ascertainable by one skilled in the art and could be made without departing from the scope disclosed herein.

Many modifications and other embodiments of the disclosure set forth herein will come to mind to one skilled in the art to which these embodiments pertain having the benefit of teachings presented in the foregoing descriptions and the associated figures. Although the figures only show certain components of the apparatuses and systems described herein, it is understood that various other components may be used in conjunction with the components and structures disclosed herein. Therefore, it is to be understood that the disclosure is not to be limited to the specific embodiments disclosed and that modifications and other embodiments are intended to be included within the scope of the appended claims. For example, the various elements or components may be combined, rearranged, or integrated in another system or certain features may be omitted or not implemented. Moreover, the steps in any method described above may not necessarily occur in the order depicted in the accompanying drawings, and in some cases one or more of the steps depicted may occur substantially simultaneously, or additional steps may be involved. Although specific terms are employed herein, they are used in a descriptive sense only and not for purposes of limitation.

The invention claimed is:

1. An apparatus for sensing a force applied by an external source in a fluid monitoring tube, the apparatus comprising:
   a force sensing device;
   signal conditioning circuitry configured to be electrically coupled to the force sensing device; and
   a housing configured to enclose the force sensing device and the signal conditioning circuitry,
   wherein the housing comprises a snap structure configured to attach the housing to a base plate and retain the force sensing device and the signal conditioning circuitry in the housing,
   wherein the housing defines a coupling interface configured to provide a path for the force to be transferred from the fluid monitoring tube to the force sensing device through a coupling,
   wherein the force sensing device comprises an annular ring structure having an outer diameter,
   wherein the coupling interface is a radial seal ring structure configured to engage the outer diameter of the annular ring structure of the force sensing device, and
   wherein the base plate comprises one or more push structures configured to push on a substrate to press fit the annular ring structure of the force sensing device in the coupling interface of the housing.

2. The apparatus of claim 1, wherein the coupling interface is an aperture in the housing.

3. The apparatus of claim 1, wherein the annular ring structure is a metal ring.

4. The apparatus of claim 1, wherein the force sensing device is configured to be disposed on a first surface of the substrate.

5. The apparatus of claim 4, wherein the force sensing device comprises a pressure range gauge sense die, the pressure range gauge sense die adhesively attached to the first surface of the substrate.

6. The apparatus of claim 5, wherein the annular ring structure is coupled to the first surface of the substrate such that the pressure range gauge sense die is positioned within the annular ring structure.

7. The apparatus of claim 4, wherein the substrate comprises a second surface opposite the first surface, wherein the signal conditioning circuitry is configured to be disposed on the first surface of the substrate, and wherein the apparatus further comprises:
   a plurality of electrical contact pads disposed on the second surface of the substrate; and
   a plurality of wedge terminals configured to mechanically couple a plurality of electrical cables to the plurality of electrical contact pads.

8. The apparatus of claim 1, wherein the coupling is a gel-based coupling comprising a gel.

9. The apparatus of claim 8, wherein the gel is a biocompatible room-temperature vulcanizing (RTV) material.

10. The apparatus of claim 9, wherein the gel is silicone.

11. A system for sensing a force applied by an external source in a fluid monitoring tube, the system comprising:
    a force sensing assembly, the force sensing assembly comprising:
       a force sensing device;
       signal conditioning circuitry configured to be electrically coupled to the force sensing device; and
       a substrate, the substrate comprising a first surface and a second surface opposite the first surface,
       wherein the force sensing device and the signal conditioning circuitry are each disposed on the first surface of the substrate and a plurality of electrical contact pads is disposed on the second surface of the substrate, and
       wherein the force sensing device comprises an annular ring structure having an outer diameter;
    a housing configured to enclose the force sensing assembly,
       wherein the housing defines a coupling interface, and
       wherein the coupling interface is a radial seal ring structure configured to engage the outer diameter of the annular ring structure of the force sensing device; and
    a base plate,
       wherein the base plate comprises one or more push structures configured to push on the substrate to press fit the annular ring structure of the force sensing device in the coupling interface of the housing.

12. The system of claim 11, wherein the substrate is a printed circuit board (PCB).

13. The system of claim 11, wherein the plurality of electrical contact pads comprise a plurality of wedge terminals.

14. The system of claim 13, wherein the plurality of wedge terminals are configured to mechanically couple a plurality of electrical cables to the plurality of electrical contact pads.

15. The system of claim 11, wherein the housing comprises one or more snap structures configured to attach the housing to the base plate and retain the force sensing assembly in the housing.

16. The system of claim 15, wherein the one or more snap structures are configured to apply pressure to a plurality of electrical cables against a plurality of wedge terminals mounted to the second surface of the substrate, such that the plurality of electrical cables engage the plurality of wedge terminals to form an electrical connection to one or more external devices.

17. The system of claim 15, wherein the base plate comprises one or more cable wire guides configured to support a plurality of electrical cables.

* * * * *